United States Patent
Caserta et al.

(10) Patent No.: US 7,382,975 B2
(45) Date of Patent: Jun. 3, 2008

(54) EVAPORATOR DEVICE FOR ACTIVE SUBSTANCES WITH FAN

(75) Inventors: Andrea Caserta, Barcelona (ES); Ruben Garcia Fabrega, Barcelona (ES); Pere Casas Colomer, Barcelona (ES); Joan Gusi Hidalgo, Barcelona (ES); Cedric Morhain, Barcelona (ES)

(73) Assignee: Zobele Espana, S.A. (ES)

( * ) Notice: Subject to any disclaimer, the term of this patent is extended or adjusted under 35 U.S.C. 154(b) by 0 days.

(21) Appl. No.: 10/519,424

(22) PCT Filed: Sep. 14, 2004

(86) PCT No.: PCT/ES2004/000400

§ 371 (c)(1), (2), (4) Date: Dec. 22, 2004

(87) PCT Pub. No.: WO03/103387

PCT Pub. Date: Dec. 18, 2003

(65) Prior Publication Data

US 2006/0120701 A1    Jun. 8, 2006

(51) Int. Cl.
F24F 6/00 (2006.01)
F24F 6/08 (2006.01)

(52) U.S. Cl. .................... 392/395; 392/392

(58) Field of Classification Search ........ 392/386–396; 261/139, 142, DIG. 65; 219/482–493
See application file for complete search history.

(56) References Cited

U.S. PATENT DOCUMENTS

| | | | |
|---|---|---|---|
| 4,629,604 A * | 12/1986 | Spector | 422/124 |
| 6,361,752 B1 * | 3/2002 | Demarest et al. | 422/306 |
| 6,563,091 B2 | 5/2003 | Viera | |
| 6,603,924 B2 | 8/2003 | Brown et al. | |
| 6,661,967 B2 | 12/2003 | Levine et al. | |
| 6,859,615 B2 * | 2/2005 | Yip et al. | 392/395 |
| 6,931,202 B2 * | 8/2005 | Pedrotti et al. | 392/395 |
| 2004/0145067 A1 | 7/2004 | Millan | |
| 2005/0001337 A1 * | 1/2005 | Pankhurst et al. | 261/104 |

FOREIGN PATENT DOCUMENTS

EP    0689766 A1    1/1996
WO    WO 03103387 A2    12/2003

OTHER PUBLICATIONS

International Search Report dated Dec. 10, 2004 for PCT Application No. PCT/ES 2004/0000400 (3 pgs.).

* cited by examiner

Primary Examiner—Sang Paik
(74) Attorney, Agent, or Firm—Fulwider Patton LLP

(57) ABSTRACT

Incorporates a device for active substances (3) which has a wick (6) and a first heating resistor (8) for operating the diffuser on normal system. It also has a single button (12) connected through an electronic circuit (10) to an additional second heating resistor (9) located in the same channel and after the first heating resistor (8) in the vicinity of the wick (6). Activation of the button (12) determines the switching on of the second heating resistor (9) and can also activate at the same time a fan (4) or even based on a fan speed (4) increase the same, moving from normal operating mode to boost mode in which a substantial and instant increase in evaporation and diffusion of the active substances is produced.

11 Claims, 3 Drawing Sheets

EVAPORATOR DEVICE FOR ACTIVE SUBSTANCES WITH FAN

RELATED APPLICATIONS

This application claims the benefit of International Application No. PCT/ES2004/000400, filed Sep. 14, 2004.

OBJECT OF THE INVENTION

The present invention relates to an evaporator device for active substances, such as fragrances, insecticides or others, of the type incorporating a fan and means of heating which are suitable for the diffusion of active substances.

The object of the invention is that the evaporator device incorporates means of operation that allow, simply and as required by the user, a rapid response to be obtained in a substantial increase in the evaporation and diffusion of the active substances for their immediate perception.

BACKGROUND OF THE INVENTION

Evaporator devices for active substances comprise in general a container device for the active substance which is diffused by means of a wick and through a casing provided with slots to the outside, the incorporation of a fan being considered as an additional means which contributes to increasing the degree of evaporation promoting the release and propulsion of the active substances.

In the case of patent WO 01/02025, a dispenser fed by a battery which incorporates a device for volatile substances located between the air inlet and outlet of the device, together with a fan which promotes the entry of air inside the device and propels it with the volatile substances to the outside, can be seen. In addition there is a cut-out system which determines the cessation of feed to the fan for a low battery level corresponding to a reduced level of volatile substances contained in the device.

Patent WO 03/086487 relates to an electric evaporator which basically incorporates a device for active substances provided with an external wick, means of heating, a fan and a grid structure through which the active substances pass to the outside. It also incorporates a rotating wheel which controls the position of the wick establishing greater or lesser closeness of the wick to the means of internal heating in order to regulate the degree of evaporation of the active substances.

In this case, the means of regulation linked with greater release of active substances is provided by the manual regulation of said wheel which varies the relative position of the wick with regard to the means of heating. Regulation is slow and the result in being noticed delayed until a period of time has elapsed.

Patent WO 00/69479 describes an evaporator device for volatile substances which includes an electric motor formed by rotor and coil arranged such that when electrical current is applied, the coin generates heat and a magnetic field is produced which causes rotation of the rotor. The volatile material is located adjacent to the rotor in order to be evaporated by the action of the heat of the coil and a fan connected to the rotor propels the active substances to the outside.

In none of the patents cited is there any mention of an evaporator device for active substances which allows any substantial and immediate acceleration of the release of active substances from a constant diffusion system such as the invention described below proposes.

DESCRIPTION OF THE INVENTION

The evaporator device for active substances with fan which constitutes the object of this invention satisfactorily meets the expectations expressed using means of activation which are activated from a permanent diffusion system in which there is a heating element to instantly switch on an additional heating element and in a collaboration with a fan suddenly increases evaporation of the active substances and diffusion of said substances in the atmosphere.

This activation of the fan and of the additional heating element significantly boosts the discharge to the outside of active substances, and unlike other systems they are immediately perceptible by the user.

It has been provided that the heating elements are arranged one after the other in the channel through which the airflow passes which also crosses the wick in order to in this way increase the efficiency of the drag by airflow.

Three possible embodiments of the device can be identified which have in common the incorporation of a heating element which in normal operating mode consists of a single source of heat emission which establishes a permanent diffusion system.

One possible embodiment of the device is that when the user presses the boost button this activates simultaneously: the additional heating element which establishes a full power system which increases the rate of evaporation, and the fan, the flow of which passes inside the apparatus contributing to the evaporation and diffusion of the active substances.

In a second embodiment, the fan is activated when the device is plugged in and the action on the button alone determines switching on the additional heating element.

In a third embodiment, the fan is activated, as in the second embodiment, when the device is plugged in, and the action on the button causes the additional heating element to be switched on and the speed of the fan to be increased.

During the boost mode, an illuminated indicator which indicates this operating situation lights up.

The duration of the boost mode is normally predefined and can be programmed in the electronic circuit which automatically returns the device to normal operating mode once the boost mode is complete. With this aim, the device can incorporate a timer which controls the time during which this diffusion boost situation occurs.

Another possibility for deactivating the boost mode consists of again pressing the button.

The evaporator device can also have an element connected to the wick by means of which regulation of the intensity of evaporation is carried out.

The evaporator device designed in this way has a great simplicity of structure, construction and function which allows the diffusion system to be changed by simply exerting pressure on the button, following which the user perceives practically instantly the substantial increase in the active substances.

DESCRIPTION OF THE DRAWINGS

To complement the description being carried out and with the aim of aiding better understanding of the features of the invention, in accordance with a preferred practical embodiment of the same, there is also, as an integral part of said description, a set of drawings in which by way of illustration and non-restricting the following has been represented.

PREFERRED EMBODIMENT OF THE INVENTION

Figure 1:
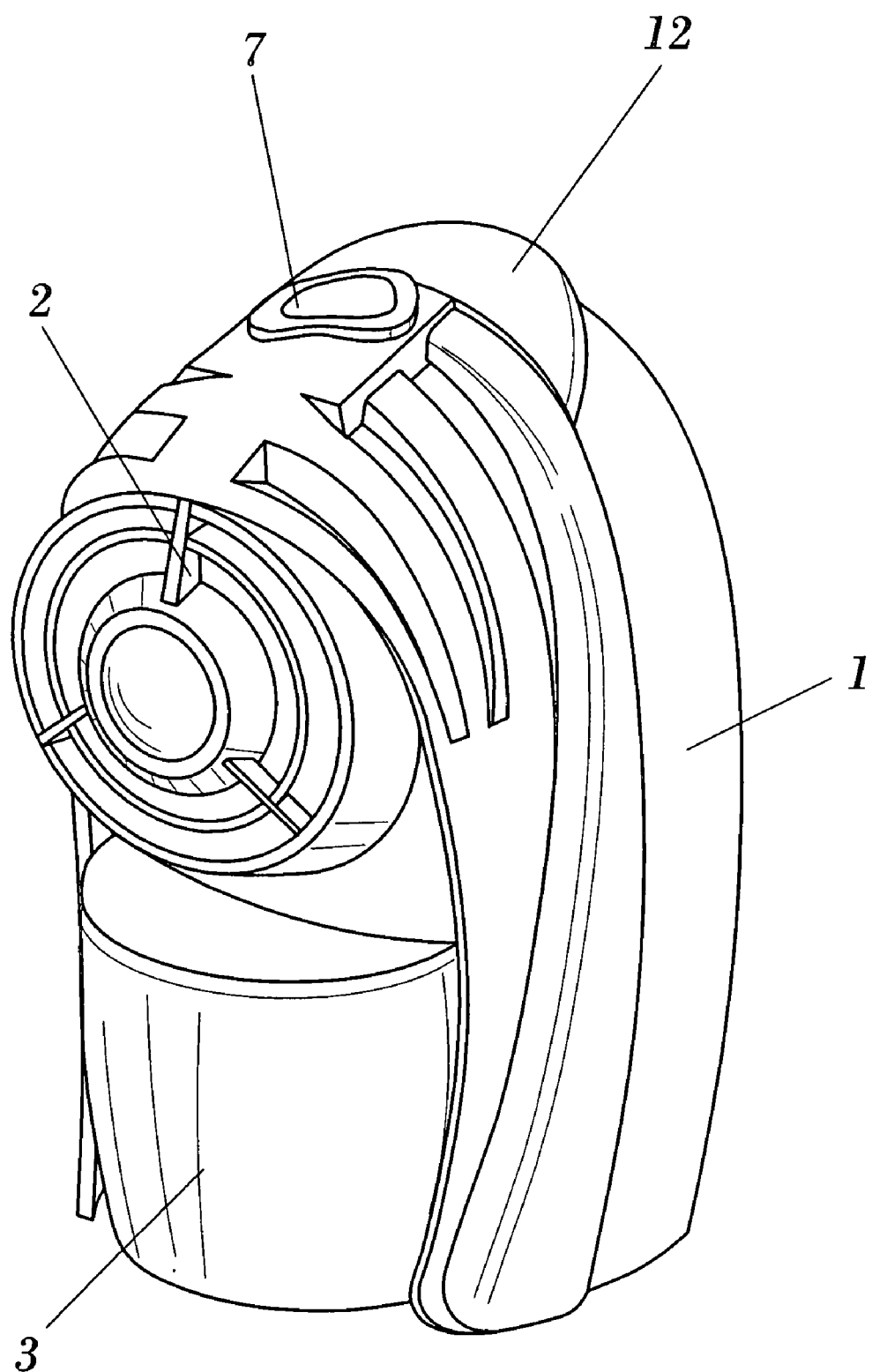
FIG. 1—Shows a view in perspective of the evaporator device for active substances with fan.

In FIG. 1 can be seen the external configuration of the evaporator device for active substances with fan which conventionally incorporates a base (1), a case (2) provided with slots for entry of air and discharge of the active substances, together with a container device for the active substances (3).

Figure 2:
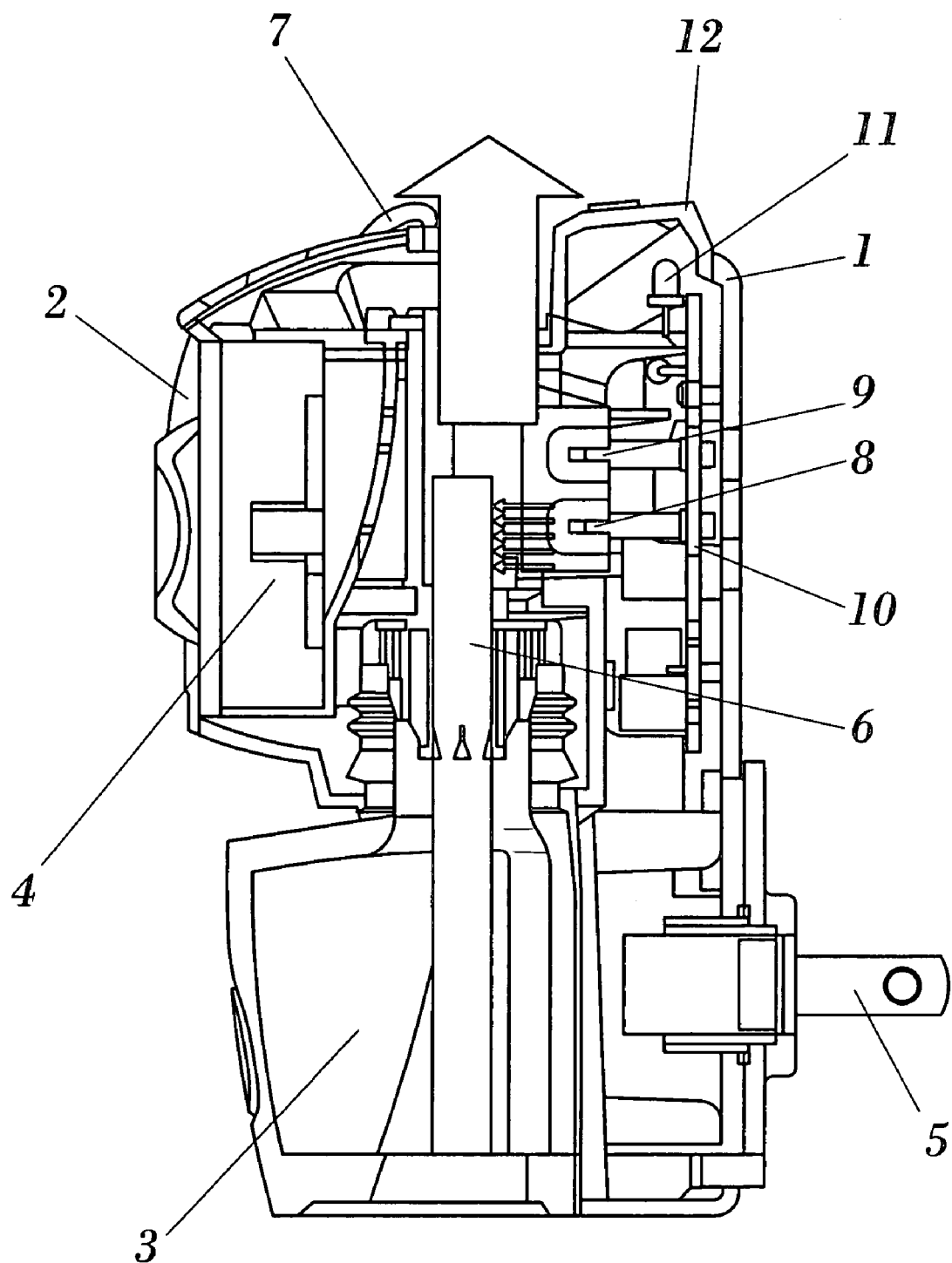
FIG. 2—Shows a sectional view of the device in which its constituent elements can be seen, in the situation corresponding to the normal operating mode of the device with a single activated resistor.
Figure 3:
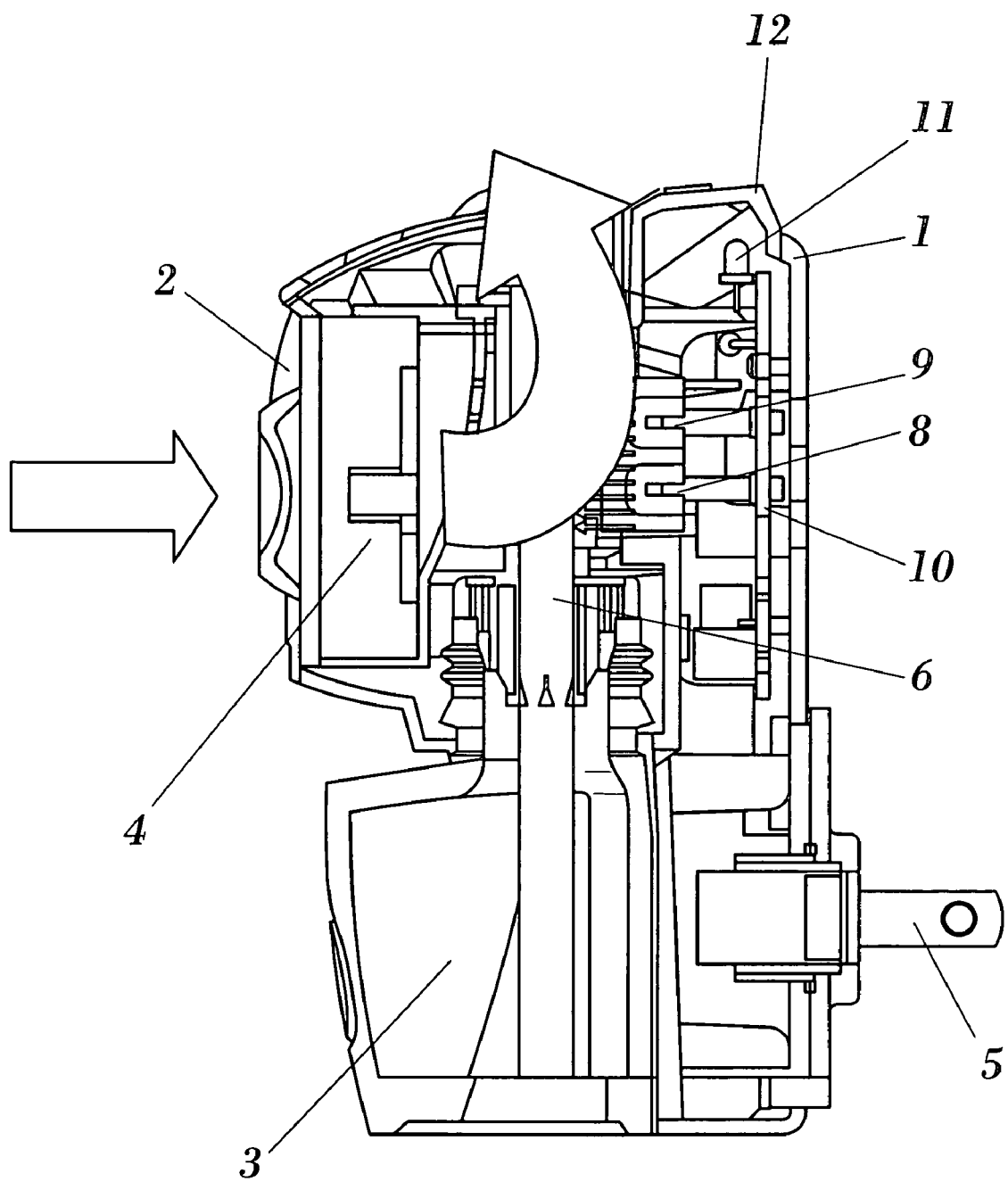
FIG. 3—Shows a sectional view of the evaporator device in the activation situation of the boost mode with the additional resistor and the fan activated, the airflow generated by the fan being observed.

Inside the device, as can be seen in FIGS. 2 and 3, incorporates a fan (4), the wick (6) of the container device for active substances (3) which is optionally connected to an evaporation intensity regulator (7), together with the plugs (5).

In a conventional solution and for normal operation of the device, this has a first heating resistor (8) which is heated when the device is plugged in by means of its plug (5), thus diffusing the active substances to the outside.

Using the basic configuration described above, the diffuser device is distinguished fundamentally because it incorporates an single button (12) connected through an electronic circuit (10) to a second additional heating resistor (9) located in the same channel and after the first heating resistor (8) in the vicinity of the wick (6) which once pressed determines the change from normal operating mode to a boost operating mode with a substantial and instant increase in evaporation and diffusion of active substances.

In a first embodiment, the button (12) is also connected through the electronic circuit (10) to the fan (4), the activation of which determines the joint switching on of the second heating resistor (9) and fan (4) moving to the boost diffusion mode.

In a second embodiment, the fan (4) is connected continuously to the plugs (5) for constant speed operation when the device is plugged in, as a result of which when the button is activated it only switches on the second heating resistor (9).

In a third embodiment, the fan (4), as in the second embodiment, is activated when the device is plugged in, and the button (12) is connected through the electronic circuit (10) to means of regulating the speed of the fan (4), the activation of which determines the switching on of the second heating resistor (9) and the increase in speed of the fan (4) moving to boost diffusion mode.

Also linked to the button (12) is a luminous indicator (11) which shows the activation situation of the button (12).

The evaporator device has means of deactivation of the boost mode which consist of the button (12) which when again pressed determines the change from boost mode to normal operating mode, or in fact consist of a timer which determines operation in boost mode until a predefined period of time in which it moves to normal operating mode has elapsed.

The invention claimed is:

1. Device for evaporation of active substances comprising:
    a casing having at least one slot for the diffusion of the active substance to the outside,
    a container for containing an active substance, said container being provided with a wick having a lower portion inside the bottle and an upper portion protruding from the bottle,
    electric plugs for the connection of the device to the electric mains,
    a first heating resistor arranged inside said casing in the vicinity of said upper portion of the wick and connected to the electric plugs,
    a fan arranged in said casing for providing an airflow through the upper portion of the wick,
    a second heating resistor arranged inside said casing in the vicinity of said upper portion of the wick,
    an electric push button to electrically supply said second heating resistor and at the same time act on the speed of said fan,
    and wherein the electric push button is operable to alternatively change the operation of the device between a normal operation mode and a boost operation mode,
    wherein in said normal operation mode said first heating resistor is activated and the fan is in a first condition,
    and wherein in said boost operation mode, the second heating resistor is selectively activated in addition to said first heating resistor and the speed of the fan is increased so as to increase the evaporation and diffusion of the active substance.

2. Device according to claim 1, wherein the fan is switched on by means of the push button.

3. Device according to claim 1, wherein the fan is connected to the electric plugs and the speed of the fan is increased by means of the push button.

4. Device according to claim 2 or 3, wherein the push button is connected to the fan by means of an electronic circuit and means for regulating the speed of the fan.

5. Device according to claim 1, wherein the first and second heating resistors and the upper portion of the wick, are arranged in a channel provided in the casing for passage of the airflow.

6. Device according to claim 1, wherein the casing incorporates a case and a base provided with slots for entry of air.

7. Device according to claim 1, wherein the wick is connected to an evaporation intensity regulator.

8. Device according to claim 1, wherein a luminous indicator is connected to the push button to show the activation situation of the second heating resistor.

9. Device according to claim 1, wherein means are provided for deactivating the boost mode.

10. Device according to claim 8, wherein the means for deactivating include the push button, which when again pressed determines a change from boost mode to normal operating mode.

11. Device according to claim 9 or 10, wherein the means for deactivating includes a timer which determines a change from boost mode to normal operating mode after a predefined period of time.

* * * * *